US009370670B2

(12) United States Patent
Henning et al.

(10) Patent No.: US 9,370,670 B2
(45) Date of Patent: Jun. 21, 2016

(54) GAMMA SOURCE TRACKING SYSTEM

(75) Inventors: Johan Henning, Veenendaal (NL); Bas Woudstra, Veenendaal (NL); Jeroen Schuurman, Veenendaal (NL)

(73) Assignee: NUCLETRON OPERATIONS B.V., Veenendaal (NL)

( * ) Notice: Subject to any disclaimer, the term of this patent is extended or adjusted under 35 U.S.C. 154(b) by 0 days.

(21) Appl. No.: 14/158,568

(22) PCT Filed: Jul. 19, 2012

(86) PCT No.: PCT/NL2012/050518
§ 371 (c)(1),
(2), (4) Date: Jan. 17, 2014

(87) PCT Pub. No.: WO2013/012331
PCT Pub. Date: Jan. 24, 2013

(65) Prior Publication Data
US 2014/0153701 A1 Jun. 5, 2014

(30) Foreign Application Priority Data

Jul. 20, 2011 (NL) .................................... 2007151

(51) Int. Cl.
*G01T 1/16* (2006.01)
*A61N 5/10* (2006.01)
*G01T 1/164* (2006.01)

(52) U.S. Cl.
CPC ............ *A61N 5/1001* (2013.01); *A61N 5/1027* (2013.01); *A61N 5/1048* (2013.01); *G01T 1/1644* (2013.01); *A61N 2005/1052* (2013.01)

(58) Field of Classification Search
CPC .. G01T 1/1644; A61N 5/1001; A61N 5/1027; A61N 5/1048; A61N 2005/1052
See application file for complete search history.

(56) References Cited

U.S. PATENT DOCUMENTS

| | | | |
|---|---|---|---|
| 3,840,747 A * | 10/1974 | Macovski | 250/369 |
| 5,374,824 A * | 12/1994 | Chaney et al. | 250/363.02 |
| 6,847,838 B1 | 1/2005 | Macey et al. | |
| 7,365,334 B1 * | 4/2008 | Gordon | 250/363.04 |
| 2004/0037394 A1 | 2/2004 | Kuroda et al. | |

(Continued)

FOREIGN PATENT DOCUMENTS

JP 60-021426 A 2/1985

OTHER PUBLICATIONS

International Search Report, issued by the European Patent Office, mailed May 12, 2012, 3 pages.

*Primary Examiner* — Yara B Green
(74) *Attorney, Agent, or Firm* — Finnegan, Henderson, Farabow, Garrett & Dunner, LLP

(57) ABSTRACT

An embodiment of the present disclosure is directed to a radioactive source tracking system adapted to determine in real time a spatial position of a gamma source in a volume, including a set of spatially distributed position sensitive detectors operable in real time arranged about the volume. The system includes a real time computer system adapted to calculate the spatial position per time stamp of the gamma source in the volume based on respective signals generated by the position sensitive detectors. In addition, the radioactive source is represented by a 3D or 4D data stream in real time. Other embodiments of the present disclosure are directed to a method for tracking a radioactive gamma source and a computer program product for causing a processor to determine a real time 3D or a 4D spatial position of a gamma source.

21 Claims, 9 Drawing Sheets

(56) References Cited

U.S. PATENT DOCUMENTS

| | | | |
|---|---|---|---|
| 2007/0093711 A1* | 4/2007 | Hoheisel et al. | 600/407 |
| 2007/0129593 A1 | 6/2007 | Gueye et al. | |
| 2007/0140427 A1* | 6/2007 | Jensen et al. | 378/98.12 |
| 2007/0205373 A1 | 9/2007 | Kornblau et al. | |
| 2009/0014015 A1 | 1/2009 | Tutar et al. | |

* cited by examiner

GAMMA SOURCE TRACKING SYSTEM

CROSS REFERENCE TO RELATED APPLICATIONS

This application is a national phase application of International Application No. PCT/NL2012/050518, filed on Jul. 19, 2012, which claims the benefit of priority of NL Application No. 2007151, filed on Jul. 20, 2011. Each of these applications is herein incorporated by reference in their entireties.

FIELD OF THE INVENTION

The invention relates to a radioactive source tracking system adapted to determine a spatial position of a gamma source in a volume. The invention further relates to a method for radioactive source tracking for determining a spatial position of a gamma source in a volume.
The invention still further relates to a computer program product for enabling radioactive source tracking for determining a spatial position of a gamma source in a volume.

BACKGROUND OF THE INVENTION

In clinical practice brachytherapy application are gaining importance. In the course of a brachytherapy treatment a radioactive source, usually a gamma emitter, is introduced into a target volume of a patient. The radioactive source may be introduced manually or using an afterloader device. Generally, the afterloader device is used for providing the radioactive source or sources inside the patient for a given (short) period of time inside pre-positioned catheters. In such a case, the gamma source may be a high dose rate source or a low dose rate source. Alternatively, the sources (seeds) may be provided inside the target volume of the patient for a prolonged (several hours) or permanent dwelling. Such sources may be low dose rate sources.

It is a disadvantage of the contemporary brachytherapy that the actual source position inside the volume is verified indirectly. For example, generally suitable X-ray imaging may be used for determining the position of the source bodies inside the patient (or a catheter introduced inside the patient). However, such approach may be not sufficiently accurate or reliable in certain circumstances, for instance when a train of sources is being provided, the active rods being interleaved with non-active spacers.

SUMMARY OF THE INVENTION

It is an object of the invention to provide an improved gamma source tracking system. In particular, it is an object of the invention to provide a gamma source tracking system capable of determining real time the actual position in real time of the gamma source based on the radiation emitted by the gamma source.

To this end the radioactive source tracking system adapted to determine in real time a spatial position of a gamma source in a volume, according to an aspect of the invention, comprises a set of spatially distributed position sensitive detectors (PSD) operable in real time arranged about the volume, a real time computer system adapted to calculate the spatial position per time stamp of the gamma source in the said volume based on respective signals generated by said PSD's, wherein the radioactive source is represented by a 3D or 4D data stream in real time.

It is found to be particularly advantageous to carry out the gamma source tracking by using a set of radiation detectors provided in a space comprising the volume wherein the gamma sources are expected to dwell. The detectors may be mounted on a ceiling, for example. To have the real time position determined, the radiation detector must measure the spatial vector in real time. To achieve this real time spatial vector the PSD, position sensitive device, is essential. The PSD measures the center of gravity of the incident light on the sensor in real time. Since the PSD is an analog sensor the accuracy is only determined by an Analog to Digital converter. The real time incident radioactive radiation is converted to visible light by the fast scintillator to maintain the real time detection with sufficient light yield. The electronics generates instantaneously spatial 2D vectors per time stamp so that with a fast computer program the 3D position per time stamp is obtained. The result is a real time data stream in 4D coordinates which follows the radioactive source in the patient. It will be appreciated that a Position Sensing Device (PSD) is a sensor that detects the position of a light spot on its surface. Generally, there a two types of PSD's, a discrete PSD and the isotropic PSD. Both are known in the art and will not be explained in detail here. It will be appreciated that it is possible to use either a discrete or the isotropic PSD for implementing the invention. However, the isotropic PSD may have a higher resolution, which is advantageous for tracing miniature gamma sources.

For example, in a particular embodiment, a spatial position of a gamma source with respect to the isocenter of the work area may be determined. It is found, that suitable calculation of the position of the gamma source may be carried out using triangulation. With this method, a position of a point can be determined through measuring the angles from that point to two fixed points at the end of a fixed baseline. The triangulation formula is defined as:

$$\text{Distance } d = \frac{\text{length baseline} \times (\sin(\alpha) \times \sin(\beta))}{\sin(\alpha + \beta)}$$

The formula must be executed two times. The first time the exact coordinates of the isocenter have to be calculated. The result will be stored in the PC with the calibration data. The formula above has to be filled in the following way:

$$\text{Distance } d_{iso} = \frac{\text{base} \times (\sin(\alpha) \times \sin(\beta))}{\sin(\alpha + \beta)}$$

Where α=angle of sensor1 to ceiling and β=angle sensor2 ceiling.

The ceiling is the wall where the sensor is installed on. The underlying geometry of the system, corresponding to the above equations, is schematically presented in FIG. 1.

$$\text{Distance } d_{source} = \frac{Base_{total} \times (\sin(\alpha_y) \times \sin(\beta_y))}{\sin(\alpha_y + \beta_y)}$$

Where:

$\alpha_y$=angle in y-axis of sensor1 and:

$\beta_y$=angle in y-axis of sensor2

In clinical applications, usually the patient is lying on a table. Accordingly, the radiation detectors from the set may be provided at respective positions about the table. It will be appreciated that the radiation detectors may be arranged on the table, or at a suitable distance from it. It is found that optimal results regarding source tracking sensitivity and accuracy may be obtained when the expected source-detector distance is about 1-2 meters.

Accordingly, the radiation source tracking system according to the invention provided sensitive and reliable means for enabling direct verification of the actual radioactive source position in the patient. The radiation source tracking must be real time since the radioactive source moves with a certain speed through the patient during treatment. More in particular, the radiation source tracking system according to the invention enables direct verification of the dose delivery to the patient. The accuracy of the delivered dose is based on calculations of a suitable planning system based on water model of a patient. Preferably, the source tracking system according to the invention provided the spatial source position in room coordinates. However, other notation, such as relative to a target area to be irradiated, is possible as well.

In an embodiment of the radioactive source tracking system according to the invention for the set of spatially distributed radiation analogue detectors are used, which are adapted to generate real time spatial vectors of the gamma source.

It is found that by applying the above method of triangulation the proper data vectors may be generated thereby enabling a 3D or a 4D real In a further embodiment of the system, each position sensitive device is combined with a pinhole in a fixed geometry.

It is found to be particularly suitable to use the pin-hole detectors for enabling the gamma source tracking. Because the pinhole detector is adapted to allow only a narrow beam of radiation to access a radiation sensitive material, the set of such pinhole detectors may be used to deconvolute the resulting signals for back-projecting the source in space.

The pinhole detector may comprise a radiation shielding housing provided with a hole, a light shield covering the hole, a scintillator crystal for generating scintillation light upon detection of an incoming photon, a position sensitive device, PSD, by which the scintillator is preferably placed as close as possible to the PSD. An embodiment of a pinhole detector is discussed in more details with reference to FIGS. 1 and 2.

In a further embodiment, the pinhole detector may further comprise a motorized gamma shutter for covering the pinhole.

It is found to be advantageous to provide a further motorized shutter, such as a wedge, for covering the pinhole of the detector's housing. Such configuration may enable measuring a noise signal which may be used either for calibration purposes or for purposes of increasing the signal to noise ratio during actual source tracking procedure.

In a still further embodiment of the tracking system according to the invention the radiation detectors comprise respective arrays of a radiation sensitive material.

Although it is possible to provide a suitable number of miniature radiation detectors for enabling the gamma source tracking, it is found to be advantageous to utilize array detectors, for calculating the source-detector disposition for back-projecting. It is found that two arrays of radiation detectors may be sufficient for enabling accurate and reliable source tracking in real time.

It will be appreciated, that the expected spatial position of the volume conceived to carry the gamma sources is known. Accordingly, the respective arrays may be mounted substantially facing a flux of gamma rays expected to emanate from the volume. This configuration will be explained in more detail with reference to FIG. 3.

In the radioactive source tracking system according to a further aspect of the invention the computer system is further adapted to calculate the actual dose distribution in the volume based on the determined spatial position of the source.

Provided the determined position of the radioactive sources is given in room coordinates, the radiation planning system, operable in room coordinates may import the source position data and may in real time calculate the actual dose delivered to the patient. Accordingly, a high precision brachytherapy may be achieved. This may have an advantageous consequence of reducing margins for delineating the target area, which causes advantageous reduction of the dose delivered to the healthy tissue.

A method for tracking a radioactive gamma source for determining a spatial position of the source delivered to a volume, according to the invention, comprises the steps of:
  measuring respective signals of a set of spatially distributed position sensitive detectors (PSD) operable in real time and arranged about the volume,
  using a real time computer system to calculate the spatial position per time stamp of the gamma source in the said volume based on respective signals generated by said PSD's,
  representing the radioactive source by a 3D or 4D data stream in real time.

A computer program product according to the invention comprises instructions for causing a processor to determine a real time 3D or 4D spatial position of a gamma source in a volume per time stamp based on data acquired by a set of spatially distributed position sensitive detectors (PSD) operable in real time. Preferably, the computer program further comprises instructions for causing the processor to calculate the effective dose distribution in the volume based on the determined spatial position of the source in the volume.

These and other aspects of the invention will be discussed with reference to Figures, wherein like reference numbers refer to like elements. It will be appreciated that the figures are provided for illustrative purposes only and may not be used for limiting the scope of the appended claims.

DETAILED DESCRIPTION OF THE DRAWINGS

Figure 1A:
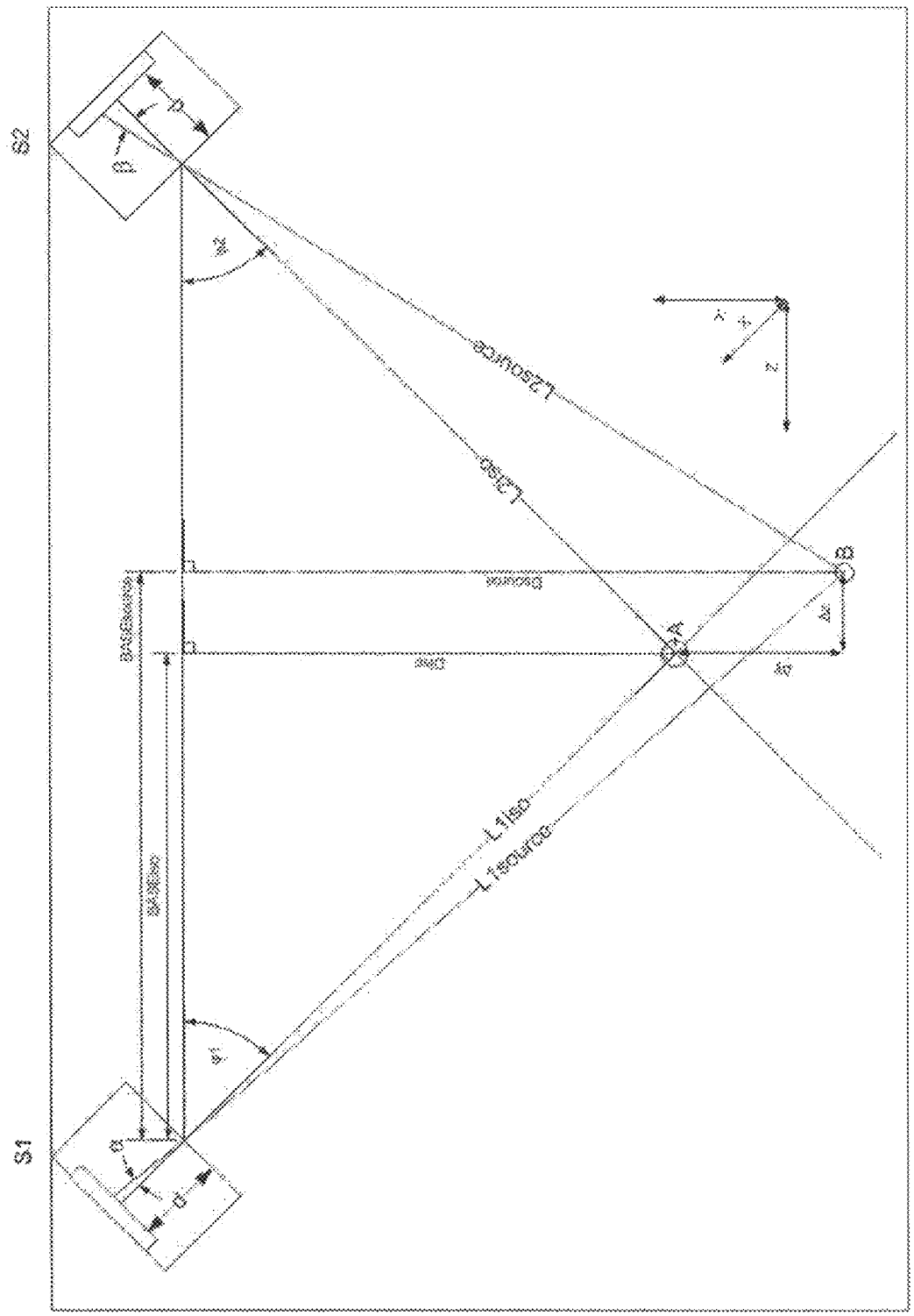
FIG. 1a presents in a schematic way an embodiment of the system geometry for applying the principle of triangulation for determining a source position is space in real time.

FIG. 1*a* presents in a schematic way an embodiment of the system geometry for applying the principle of triangulation for determining a source position is space in real time. It will be appreciated that FIG. 1 shows a 2-D drawing of a 3-D geometry. The orientation of the three Cartesian axes is shown on the bottom of FIG. 1*a*. Point A shows the isocenter of the work area (may also be referred to as the volume of interest, or the volume). The PSD sensors cooperate with a preceding scintillation detector (not shown) and generate a voltage that is proportional to the location of the light beam on the detection area of the PSD. With a pre-known formula the voltage levels are transformed to x and y coordinates. These x and y coordinates will then be used to determine the exact position of the gamma source.

The depth d between the pinhole and the surface of the PSD is a constant. It is defined in the design of the sensor. With this constant, the angle between the center of the PSD and the x and y position of the light beam can be calculated. The formula is as follows:

$$\text{angle } \alpha = \operatorname{atan}\left(\frac{\Delta y}{\text{depth pinhole } d \text{ to } PSD}\right)$$

This formula must be calculated four times to get four separate angles. With the calculated angles the triangulation can be performed. The parameters used in these formulas are shown above in FIG. 1*a*.

$$\text{Distance } d_{source} = \frac{Base_{total} \times (\sin(\alpha_y) \times \sin(\beta_y))}{\sin(\alpha_y + \beta_y)}$$

Where:

$\alpha_y$=angle in *y*-axis of sensor1 and:

$\beta_y$=angle in *y*-axis of sensor2

In this example the triangulation is performed on the angles calculated on the y-axis. With the length of $d_{source}$ calculated, the movement of the source on the y-axis can be determined. The formula for this calculation is:

$$\Delta y = d_{iso} - d_{source}$$

Next parameter to be determined is $\Delta z$. This parameter tells how much the gamma source has moved from left to right (z-axis). This movement is determined by the distance between $base_{iso}$ and $Base_{source}$. The angles between the sensor and the baseline ($\phi_1$ and $\phi_2$) are a constant and the length $d_{iso}$, which is calculated before, the length of $Base_{iso}$ can be calculated.

$$base_{iso} = \frac{d_{iso}}{\tan(\varphi_1)}$$

The next step is to calculate $base_{source}$.

$$base_{source} = \frac{d_{source}}{\tan(\varphi_1 + \alpha_y)}$$

$\Delta z$ is then defined through:

$$\Delta z = base_{source} - base_{iso}$$

Figure 1B:
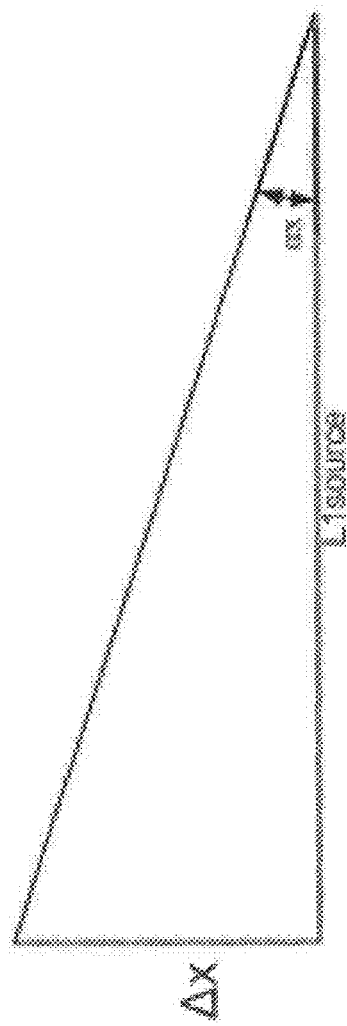
FIG. 1b presents in a schematic way an embodiment of an x-axis triangle used for computations.

The 2-D coordinates are now determined. The coordinate along the x-axis is calculated by placing a triangle on line $L_{1-source}$. FIG. 1*b* shows this triangle with all the sides defined.

The side $L_{1-source}$ is determined by the angle $\alpha_y$ and $d_{source}$. The formula is the following:

$$L_{1-source} = \frac{d_{source}}{\sin(\varphi_1 + \alpha_y)}$$

Using the tangent formula the $\Delta x$ is determined. The formula below is used to calculate this deviation:

$$=x=L_{1-source} \times \tan(\alpha_x)$$

Now all three coordinates are known and the position of the gamma source in real time is calculated.

Figure 2:
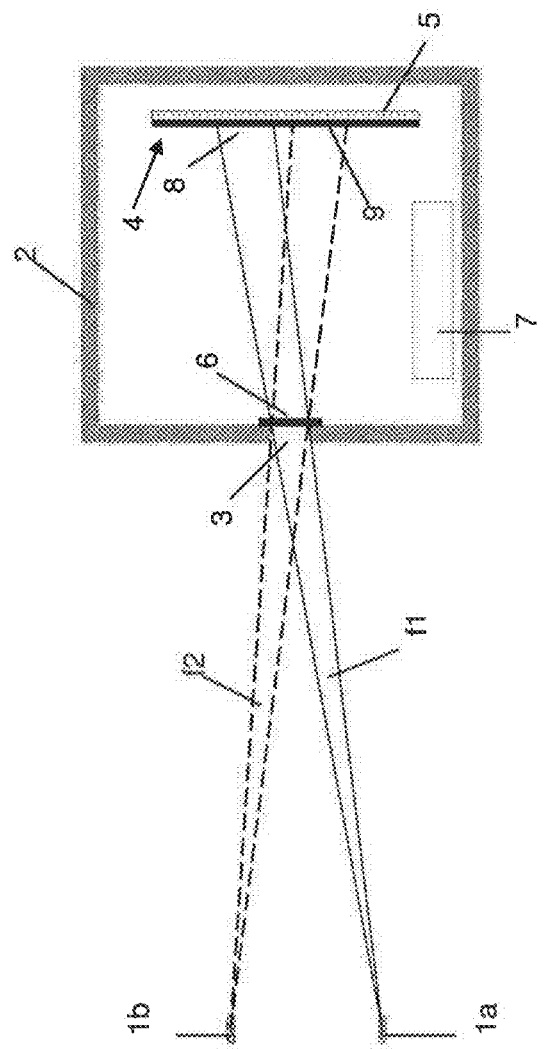
FIG. 2 presents in a schematic way an embodiment of a pinhole detector for use in the radiation source tracking system according to an aspect of the invention.

FIG. 2 presents in a schematic way an embodiment of a pinhole detector for use in the radiation source tracking system according to an aspect of the invention. In accordance with an aspect of the invention a suitable detector material 4 may be provided inside a radiation shielding housing 2. In the housing 2 a pin hole 3 may be provided for allowing radiation emanating from the source 1*a* to access the detector 4. For the detector material a scintillator crystal may be used. In order to reduce influence of ambient light on the detector readings, the pin hole 3 may be covered with a suitable, preferably opaque, light shielding 6.

The detector material 4 may be provided in contact with a suitable position sensitive device 5, adapted to generate a signal in dependence on the origin of the generated light by the scintillator detector. It will be appreciated that for a different position of the source (see 1*b*) having a different radiation flux f2, a different portion 9 of the array-detector 4 will be activated, compared to the portion 8 activated by the source 1*a* having the flux f1. Preferably, the output of the position sensitive device 5 is connected to suitable signal processing electronics 7. The electronics 7 may be adapted to supply a suitable further signal to a computer (not shown) which is adapted for determining the spatial position of the source 1*a* based on the signal delivered by the detector 4.

Figure 3:
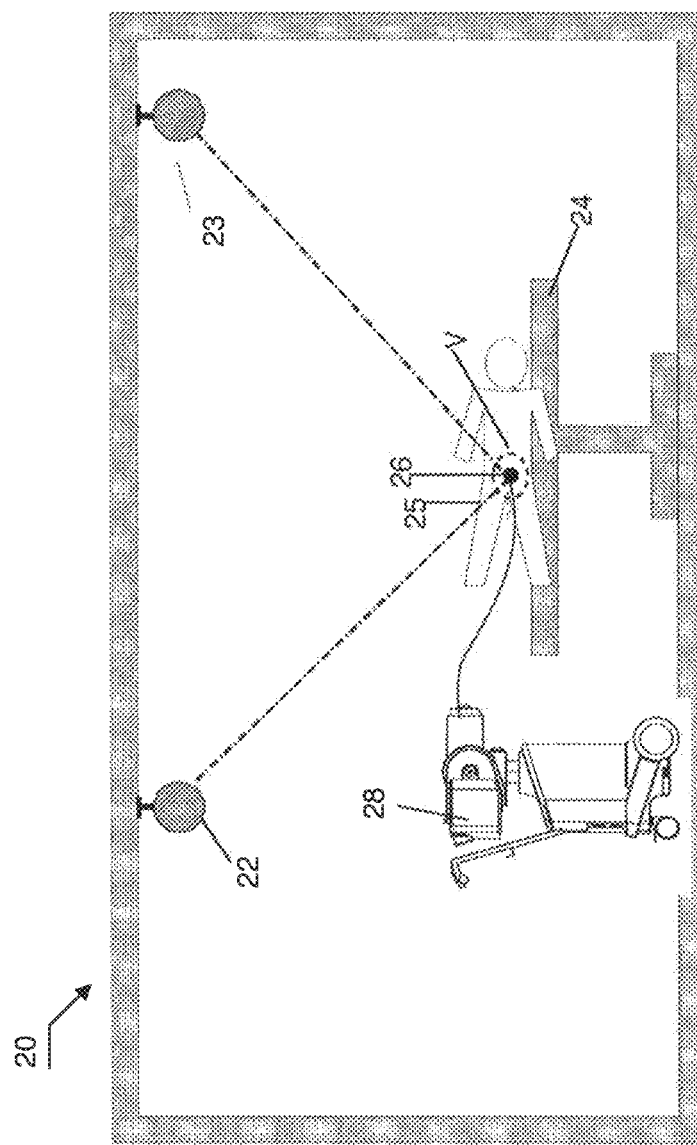
FIG. 3 presents in a schematic way an embodiment of the radiation source tracking system comprising the array-detectors.

FIG. 3 presents in a schematic way an embodiment of the radiation source tracking system comprising the array-detectors. In this particular embodiment a treatment room 20 is shown. A patient 25, lying in a supine position on a table 24 is provided with a radioactive gamma source 26 using an afterloading device 28. In accordance with an aspect of the invention, the radiation source tracking system is provided using pinhole detectors 22, 23. The detectors, mounted within a suitable radiation shielding, may be mounted to a ceiling of the room 20. However, a different mounting position may be used. For example, the detectors 22, 23 may be mounted on the table 24, which may be advantageous as the flux from the source 26 reduced inversely proportional to a square of a distance to the source. Those skilled in the art will readily appreciate which optimal distance between the volume V wherein the source 2 is dwelling and the detector may be optimal for a given source activity. It will be further appreciated that the volume V may relate to a portion within a patient, or to a position within a catheter adapted to accommodate the source 26 in use.

Figure 4:
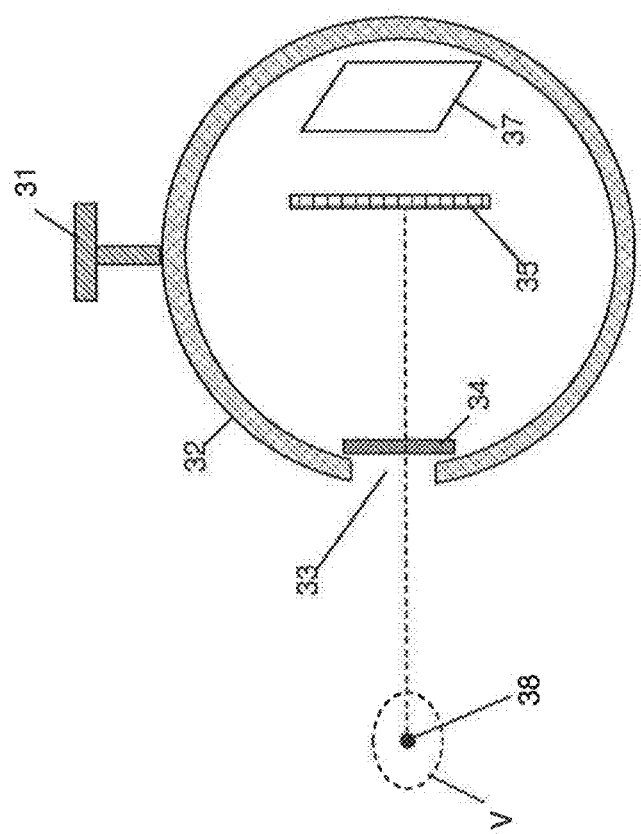
FIG. 4 presents in a schematic way an embodiment of the array-detector of FIG. 3.

FIG. 4 presents in a schematic way an embodiment of the array-detector of FIG. 3. In this particular embodiment the radiation shielding housing 32 may be mounted to a portion of the ceiling 31 of the radiation treatment room. The source 38 conceived to be tracked using the radiation tracking system according to the invention is dwelling in a prescribed volume V. The radiation emanating from the source 38 may reach the radiation sensor 35 through a pinhole 33 provided in the shielding 32. The pinhole may be further covered by an opaque material 34 for preventing ambient light to penetrate inside the pinhole detector. This reduced noise component originating from the ambient light.

The detector material 35 may comprise a suitable scintillator. The scintillator may be attached to a position sensitive device 37, which has also been discussed with reference to FIG. 2. The position sensitive device 37 is adapted to generate a signal in dependence on its activated area. In this way, the signals from the position sensitive devices provided in the set of radiation detectors as is described with reference to the foregoing, may be used for back-projecting and for determining the spatial position of the source 38 inside the volume V. It is found that using the radiation source tracking system according to the invention determination of the spatial position of the gamma source may be determined with accuracy of +−0.5 mm. The radiation source tracking system according to the invention may be set to provide a continuous update of the determined position of the source. Preferably, an update of about 25 X, Y, Z positions of the source per second is useful.

Figure 5:
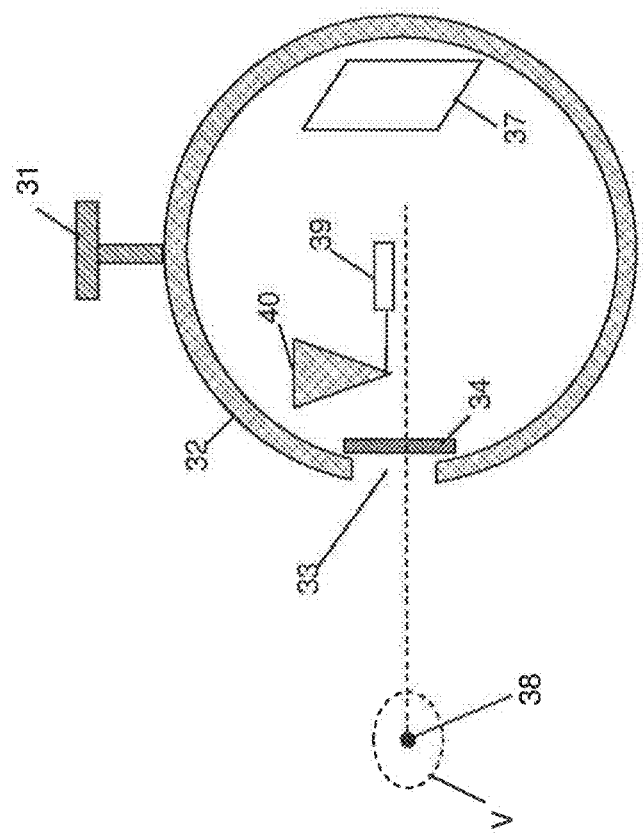
FIG. 5 presents in a schematic way a further embodiment of a pinhole detector shown in FIG. 2.

FIG. 5 presents in a schematic way a further embodiment of a pinhole detector shown in FIG. 2. In this particular embodiment the position sensitive device 37 is adapted to receive radiation from the source 38 via a pinhole 33 provided in a radiation shielding housing 32. The radiation emanating from the source may be intercepted by an opaque material 34 for reducing noise due to ambient light. In order to reduce noise due to scattered radiation penetrating the pinhole detector, a displaceable wedge absorber 40 may be provided. The wedge absorber may be displaced using a motor 39.

Figure 6:
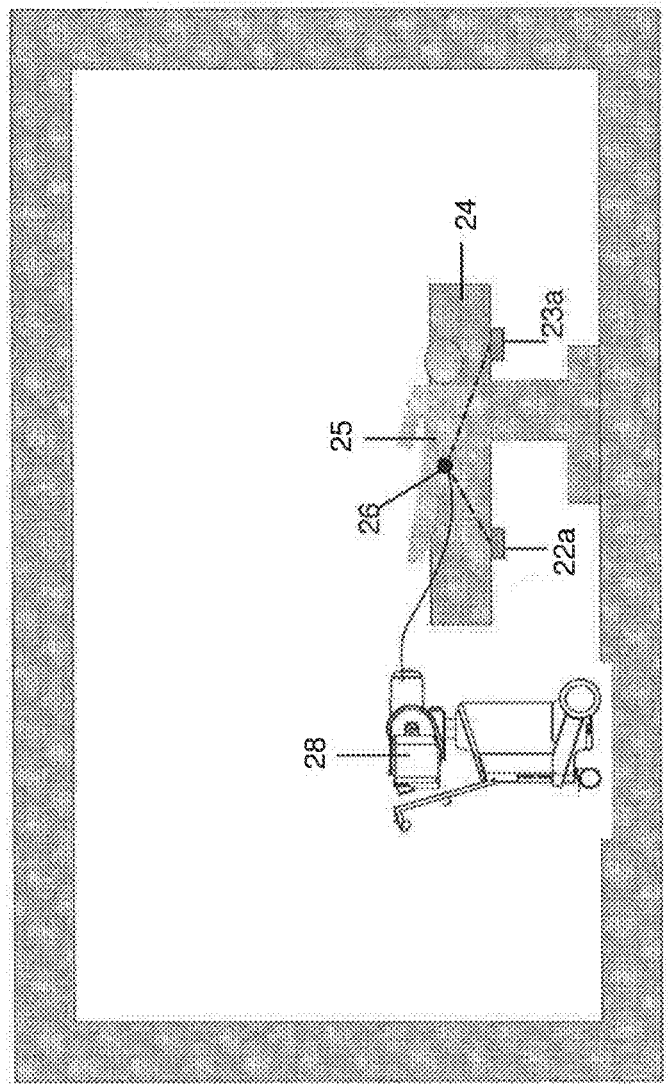
FIG. 6 presents in a schematic way a further embodiment of the radiation source tracking system according to a further aspect of the invention.

FIG. 6 presents in a schematic way a further embodiment of the radiation source tracking system according to a further aspect of the invention. In this particular embodiment the patient 25 is lying in a supine position on the table 24. A suitable radioactive source 26 is provided inside the patient using an afterloader device 28, which may be operable using high dose rate (HDR) sources or low dose rate (LDR) sources. The source 26 may be provided inside a suitable catheter (not shown) pre-positioned inside the patient 25. In accordance with the present aspect of the invention the source tracking system comprising at least two detector arrays 22a, 23a is mounted to the patient table 24. It is found that in some applications it may be advantageous to provide the source tracking system closer to the patients, for example within one meter distance from an expected source dwell location.

Figure 7:
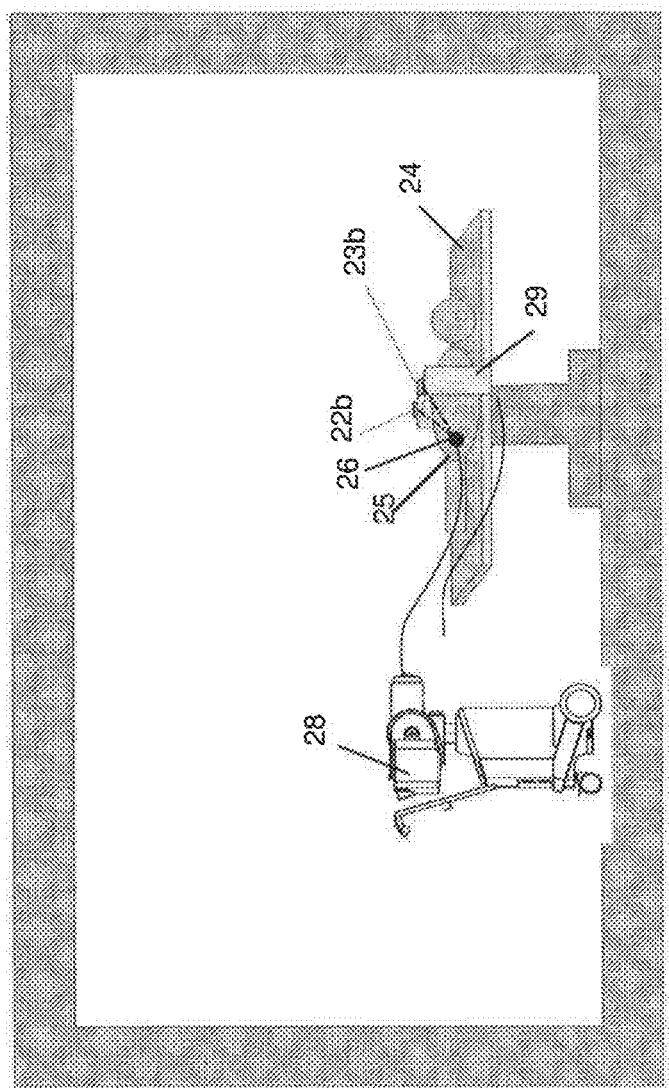
FIG. 7 presents in a schematic way a still further embodiment of the radiation source tracking system according to a still further aspect of the invention.

FIG. 7 presents in a schematic way a still further embodiment of the radiation source tracking system according to a still further aspect of the invention. In this embodiment the patient 25 is lying on the patient support table 24. The HDR or LDR source 26 is provided inside the patient using a suitable afterloader device 28. The source tracking system comprising detectors 22b, 23b is mounted to the patient support table 24 using a mounting aid 29. This embodiment is found advantageous as radiation emanating from the source 26 is not intercepted by the patient support table 24 on its way towards the detectors 22b, 23b.

Figure 8:
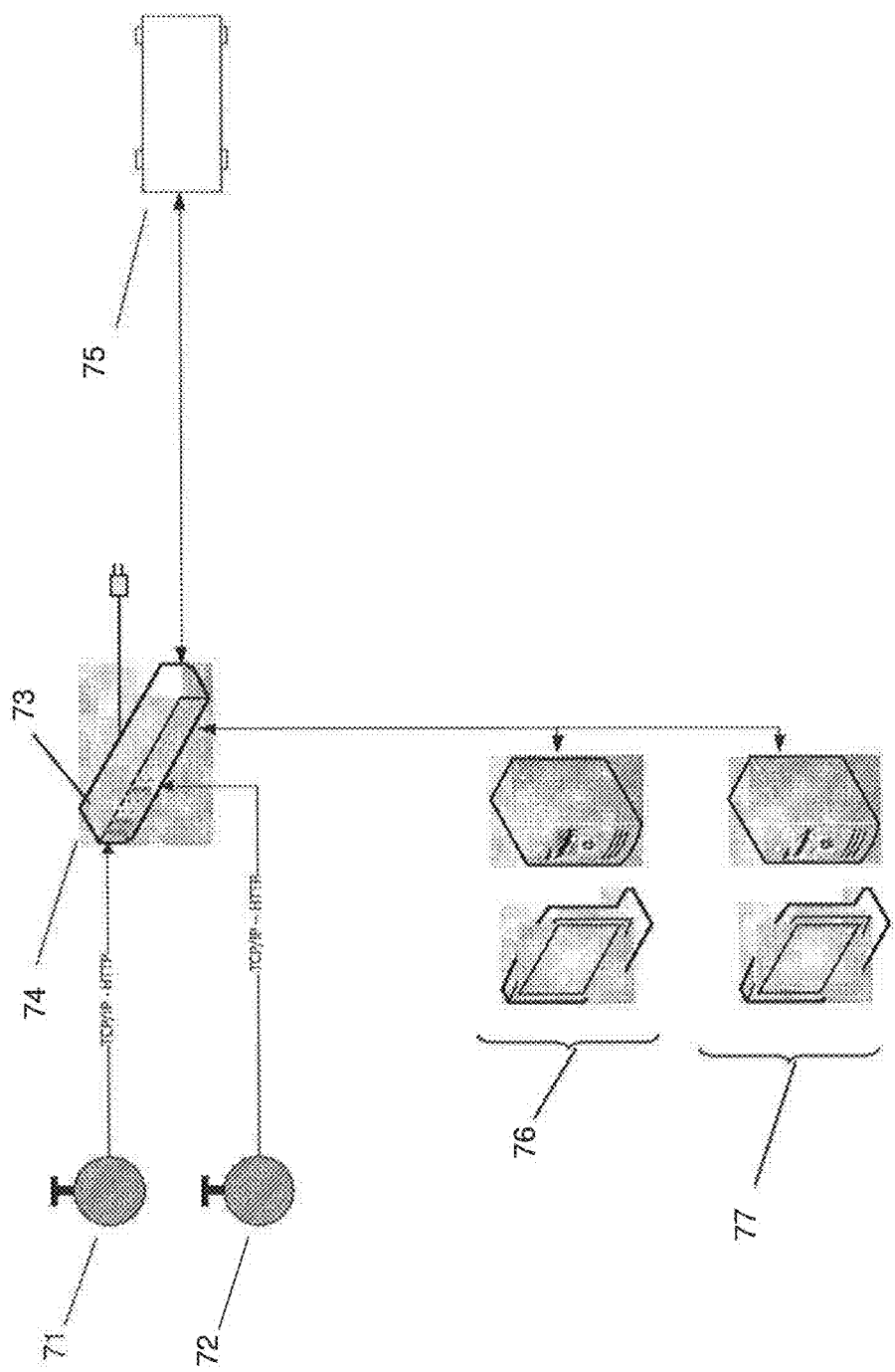
FIG. 8 presents in a schematic way an embodiment of hardware system architecture according to an aspect of the invention.

FIG. 8 presents in a schematic way an embodiment of hardware system architecture according to an aspect of the invention. It will be appreciated that there are at least two options for implementing the system according to the invention. First, the output of the PSD is connected to the field programmable gate array (FPGA) via a suitable A/D converter. It will be appreciated that in this embodiment each PSD communicates with its own FPGA. The output of the FPGA is connected to a PC. The FPGA may be arranged to only calculate the x & y coordinates of the PSD sensor itself. Not the displacement of the LED in the work area. The PC is then used to calibrate and calculate the position of the LED in the work area. The two PSD 71, 72 are placed at the sealing of the treatment room. A PoE (Power over Ethernet) switch 74 may be placed in the sealing and connected to a PC 73. The two PSD are connected to the PoE switch via Ethernet.

This embodiment has the following advantages:
The calculation of the x, y & z coordinates is performed on one central location in the system.
The system is modular. A random number of sensors can be installed; the limit is the number of IP addresses the DHCP server on the PC is configured to handle.
The calculation of the 3-D coordinates is fast, since the PC has sufficient calculation power and the necessary software libraries.
No data has to be stored offline in the FPGA.
Fast connection between the FPGA's and the PC through a standardized 100 Mbit/s Ethernet interface.
The sensors shall be supplied through PoE. This standard is EMC and ESD certified.

In the second option the system uses one FPGA to read data from two sensors. The sensors are connected with the FPGA through a SPI bus. The FPGA is calibrated to calculate the distance from the isocenter and sends the x, y and z coordinates to the PC. The PC then only shows the calculated coordinates.

This embodiment has the following advantages:
A single FPGA is necessary in the entire system which reduces the cost per sensor.
The full calculation power of the FPGA is used.

It will be appreciated that the choice between the first and the second option may depend on the demands of a particular situation. The system may further comprise an embedded PC 75 which may function as a position server. The output of the FPGA 73 may be provided to a planning system 76 for calculating the actual dose distribution inside the patient based on the real time positions of the gamma source determined using the PSD's 71 and 72. Secondly, the output of the FPGA 73 may be provided to the afterloader 77 for controlling or adapting the position of the gamma source for matching the pre-planned position. It will be appreciated that a suitable pre-planned position is established before implementing the treatment for effectuating the pre-determined treatment plan. The pre-planned source position is carried out by a suitable dose planning system based on the patient images.

While specific embodiments have been described above, it will be appreciated that the invention may be practiced otherwise than as described. The descriptions above are intended to be illustrative, not limiting. Thus, it will be apparent to one skilled in the art that modifications may be made to the invention as described in the foregoing without departing from the scope of the claims set out below.

The invention claimed is:
1. A radioactive source tracking system adapted to determine in real time a spatial position of a gamma source in a volume, the system comprising:

a set of spatially distributed position detectors operable in real time and arranged about the volume, wherein each position detector outputs vector data associated with the spatial position of the gamma source; and a processor configured to:
receive, from each position detector, data reflecting the spatial vector data,
calculate, based on the received data reflecting the respective spatial vector data, the spatial position of the gamma source in the volume; and
generate, in real time, a three-dimensional or four-dimensional data stream representative of the spatial position of the gamma source; and
update the spatial position of the gamma source at a rate of 25 updates per second.

2. The system of claim 1, wherein the position detectors are analog detectors configured to generate the vector data.

3. The system of claim 1, wherein each position detector has a geometry having a pinhole for receiving gamma rays associated with the gamma source.

4. The system of claim 3, wherein the geometry comprises a housing defining the pinhole, a light shield covering the pinhole, and a scintillator crystal for generating scintillation light upon detection of an incoming photon.

5. The system of claim 3, wherein the configuration further comprises a motorized gamma shutter for covering the pinhole.

6. The system of claim 5, wherein the scintillator crystal comprises respective arrays of a radiation sensitive material.

7. The system of claim 6, wherein the spatial position of the volume is predetermined; and
wherein the arrays are mounted to substantially face a flux of gamma rays expected to emanate from within the volume.

8. The system of claim 1, wherein the set of position detectors is located within two meters from the volume.

9. The system of claim 8, wherein the set of position detectors is located within one meter from the volume.

10. The system of claim 1, wherein the volume includes at least a portion of a patient.

11. The system of claim 1, wherein the processor is configured to calculate an actual dose distribution in the volume based on the calculated spatial position of the gamma source.

12. The system of claim 1, wherein the radioactive source forms part of a brachytherapy delivery system.

13. The system of claim 1, wherein each position detector outputs two-dimensional vector data associated with the spatial position of the gamma source, and wherein the processor is further configured to receive, from each position detector, data reflecting the two-dimensional spatial vector data, and calculate, based on the received data reflecting the respective two-dimensional spatial vector data.

14. The system of claim 1, wherein each of the spatially distributed position detectors is an isotropic position sensing device.

15. A method for tracking a radioactive source for determining a spatial position of a gamma source delivered to a volume, the method comprising:
measuring respective vector signals of a set of spatially distributed position detectors operable in real time and arranged about the volume;
calculating, based on data reflecting the respective signals generated by the position detectors, the spatial position of the gamma source in the volume;
generating, in real time with a processor, a three-dimensional or four-dimensional data stream representing the spatial position of the gamma source; and
updating the spatial position of the gamma source at a rate of 25 updates per second.

16. The method of claim 15, further comprising measuring respective two-dimensional vector signals of a set of spatially distributed position detectors operable in real time and arranged about the volume.

17. The method of claim 15, wherein each of the spatially distributed position detectors is an isotropic position sensing device.

18. The method of claim 15, wherein the position detectors are analog detectors configured to generate real-time spatial vectors of the gamma source.

19. A non-transient computer readable medium comprising program instructions that upon execution by a processor causes the processor to:
receive, from a set of spatially distributed position detectors operable in real time and arranged about the volume, data reflecting spatial vector data associated with a spatial position of the gamma source;
calculate, based on the received data reflecting the respective spatial vector data, the spatial position of the gamma source in the volume;
generate, in real time, a three-dimensional or four-dimensional data stream representative of the spatial position of the gamma source; and
update the spatial position of the gamma source at a rate of 25 updates per second.

20. The computer readable medium of claim 19, wherein execution of the instructions by the processor causes the processor to determine, in real time, the three-dimensional or four-dimensional spatial position of the gamma source in the volume based on a set of two-dimensional spatial vector data acquired by the respective set of spatially distributed position detectors.

21. The computer readable medium of claim 19, wherein execution of the instructions by the processor causes the processor to calculate an effective dose distribution in the volume based on the determined spatial position of the gamma source in the volume.

* * * * *